United States Patent [19]

Eckhardt et al.

[11] Patent Number: 5,144,040
[45] Date of Patent: Sep. 1, 1992

[54] PROCESS FOR THE PREPARATION OF 1-(ACYLAMINOALKYL)-2-IMIDAZOLINES SUBSTITUTED IN THE 2 POSITION

[75] Inventors: Georg-Wolfgang Eckhardt, Frankfurt am Main; Karl-Heinz Keil, Hanau-Mittelbuchen; Manfred Schrod, Weiterstadt, all of Fed. Rep. of Germany

[73] Assignee: Cassella Aktiengesellschaft, Frankfurt am Main, Fed. Rep. of Germany

[21] Appl. No.: 573,041

[22] PCT Filed: Mar. 1, 1989

[86] PCT No.: PCT/EP89/00197

§ 371 Date: Sep. 4, 1990

§ 102(e) Date: Sep. 4, 1990

[87] PCT Pub. No.: WO89/08106

PCT Pub. Date: Sep. 8, 1989

[30] Foreign Application Priority Data

Mar. 5, 1988 [DE] Fed. Rep. of Germany ....... 3807246

[51] Int. Cl.$^5$ .................... C07D 233/26; A61K 7/50; C11D 3/28
[52] U.S. Cl. .................................. 548/352; 548/353
[58] Field of Search ................................ 548/353, 352

[56] References Cited

U.S. PATENT DOCUMENTS 4,709,045 11/1987 Kubo et al. .................... 548/352

OTHER PUBLICATIONS

Chemical Abstracts, vol. 111, entry 7402b, 1989.

*Primary Examiner*—Patricia L. Morris
*Assistant Examiner*—Lenora Miltenberger
*Attorney, Agent, or Firm*—Connolly & Hutz

[57] ABSTRACT

In a process for preparing 2-substituted 1-(acylaminoalkyl)-2-imidazolines of the general formula I

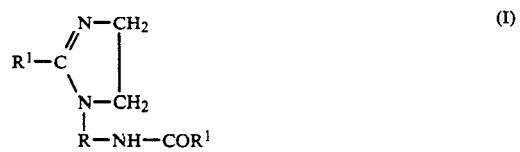

where R is an alkylene radical and $R^1$ is a fatty acid radical, for example a fatty acid and a dialkylenetriamine are reacted with one another in a molar ratio of (1.8 to 2.0):1 by initially introducing one starting material at a temperature $T_1$ and metering in the second starting material as a liquid, maintaining in the reaction mixture during the addition a temperature $T_1$ and after the addition until the start of the cyclization a temperature $T_2$ and distilling off the resulting water or alcohol via a rectification column and, after the acylation product has been formed, cyclizing in a conventional manner, $T_1$ being a temperature of 170° C. to the boiling point of the initially introduced starting material, but not higher than 250° C., and $T_2$ being a temperature of 170° to 250° C.

15 Claims, No Drawings

PROCESS FOR THE PREPARATION OF 1-(ACYLAMINOALKYL)-2-IMIDAZOLINES SUBSTITUTED IN THE 2 POSITION

The invention relates to a process for the preparation of 1-(acylaminoalkyl)-2-imidazolines substituted in the 2 position of the general formula I

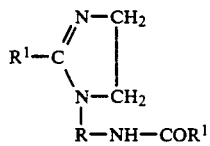

in which

R is an alkylene radical of the formula $-CH_2CH_2-$, $-CH_2CH_2CH_2-$, $-CH(CH_3)CH_2-$ or $-CH(CH_3)CH_2CH_2-$ and $R^1$ is a fatty acid radical of 7 to 25 C atoms.

Compounds of the formula I where R is ethylene and trimethylene are known and are required in particular for the preparation of the corresponding quaternized imidazolinium salts (cf. Kirk-Othmer, Encyclopedia of Chemical Technology, Third Edition, Volume 19, (1982), page 527), which in turn are important industrial surfactants. They are used in particular in the cosmetics and body care sector because they are mild and gentle to the skin. Compounds of the formula I where R is ethylene or trimethylene are also used in considerable amounts as components in the formulation of detergents and anti-corrosives.

To prepare the compounds of the formula I where R is ethylene and trimethylene, it is known to react a fatty acid of the general formula II $$R^1COOH \qquad (II)$$

which $R^1$ has the meaning already mentioned with a dialkylenetriamine of the formula III $$H_2N-CH_2-CH_2-NH-R-NH_2 \qquad (III)$$

which R is ethylene ($-CH_2CH_2-$) or trimethylene ($-CH_2CH_2CH_2-$). For complete conversion a stoichiometric molar ratio of fatty acid to dialkylenetriamine of 2.0:1 is necessary.

To prepare a compound of the formula I, for example by the typical Example 2 of the French patent specification 1,582,293, a mixture of behenic acid and diethylenetriamine is heated in a molar ratio of 2:1 in xylene in a nitrogen atmosphere under reduced pressure at 90° to 100° C. for 15 hours and, at the same time, the water of the reaction formed is distilled off azeotropically. The xylene is then distilled off under reduced pressure. Carrying out the reaction in xylene and the need to recover the xylene is complicated and makes the process more expensive, in particular as a result of the necessary work-up of the xylene-containing aqueous distillates formed.

For preparing compounds of the formula I where R is ethylene and trimethylene, it is also already known to react the fatty acid of the formula II and the dialkylenetriamine of formula III where R is ethylene and trimethylene without using a solvent. The difficulties of preparing compounds of the formula I by reacting fatty acids of the formula II with dialkylenetriamine of the formula III are in part due to the fact the reaction proceeds in two steps, in which first the dialkylenetriamine is acylated by the fatty acid and this intermediate is then converted to the compound of the formula I with ring closure, and due to the requirement that for an industrially useful process for the preparation of the compounds of the formula I, the yield of the compounds of the formula I must be high and only negligible amounts of the starting compounds and of possible acylation intermediates of the formulae IV to X $$R^1CO-NH-CH_2-CH_2-NH-R-NH_2 \qquad (IV)$$

$$H_2N-CH_2-CH_2-NH-R-NH-COR^1 \qquad (V)$$

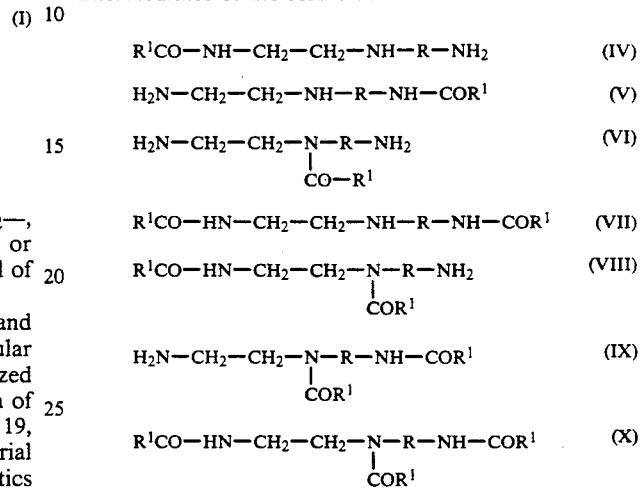

and of other imidazoline compounds, for example those of the general formula XI

must be present in the product obtained In the case where R is ethylene, the abovementioned formulae IV and V and VIII and IX are identical to one another.

The investigations by Raymond G Bistline, James W. Hampson and Warner M. Linfield in JAOCS, Vol. 60, No. 4, (April 1983), pages 823 to 828, in particular page 826, have disclosed that in the reaction of a fatty acid of the formula II with diethylenetriamine at a temperature of 90° C. first a gelatinous amine soap is formed by salt formation, which upon heating to 130° C. gives the acylation product of the abovementioned formula VI, from which then with further fatty acid upon heating at 150° C. for 6 hours an intermediate of the abovementioned formula VIII is predominantly formed. This intermediate can then be converted by heating at 150° C. under a reduced pressure of 0.2 mm Hg to the desired imidazoline of the formula I. At a total cyclization time of 8 hours, yields of 95% of the desired imidazoline of the general formula I are obtained in this process on a laboratory scale. Bistline et al. recommend going quickly through the temperature range of 90° to 125° C., in which the paste-like gel phase of amine soaps occurs. The amine soaps have a tendency towards extreme foaming. The application of this process to an industrial scale is not possible without difficulties because even small amounts of the amine soaps cause foaming of the reaction melt which is hard to control and in addition the conversion to the compounds of the general formula VIII with the elimination of water begins spontaneously above 140° C., so that in reactions carried out on a large scale with removal of the water by distillation bumping, foaming and uncontrolled distillation of compounds of the general formula III often occur and an exact molar ratio of the reaction components can only be maintained with difficulty. Therefore, in DE-Al-3,620,218, the reaction between the fatty acid of the formula II where R&hu 1 is an alkyl or alkenyl group of 8 to 22 C atoms and a dialkylenetriamine of the formula III where R is ethylene and trimethylene is controlled in such a manner that first a product is formed which predominantly consists of an imidazoline compound of the abovementioned formula XI. This imidazoline compound of the formula XI is then converted to the desired compound of the general formula I by further reaction with the fatty acid of the formula II.

In the process of DE-Al 3,620,218 for the preparation of compounds of the formula I where R is ethylene, trimethylene, 1) dialkylenetriamine where R is ethylene or trimethylene is placed together with a higher fatty acid of the formula II where $R^1$ is an alkyl or alkenyl group of 8 to 22 C atoms, or an ester thereof, in a molar ratio of fatty acid or fatty acid ester: dialkylenetriamine of 1.5:1 to 1.8:1 in a reactor and 2) the reaction is carried out at an internal temperature of 100° to 250° C. under reduced pressure and 3) the higher fatty acid or an ester thereof is added to the reaction mixture so that a molar ratio of fatty acid or fatty acid ester to dialkylenetriamine of at least 2.0:1 can be reached and 4) the reaction is continued at an internal temperature of 100° to 250° C. under reduced pressure.

According to the typical Example 1 of DE-Al 3,620,218, bovine tallow fatty acid and diethylenetriamine were heated in a molar ratio of 1.8:1 and 150° C. at a pressure of 400 mm of Hg for 3 hours. The temperature was then raised to 230° C. and maintained for 4 hours and at the same time the pressure was reduced to 30 mm of Hg. The reaction mixture was then cooled and a further 0.162 mol of bovine tallow fatty acid was added, so that a molar ratio of bovine tallow fatty acid to diethylenetriamine of 1.99:1 was reached. The mixture was then heated at 230° C. under a pressure of 30 mm of Hg for 8 hours. Accordingly, the overall reaction time was 15 hours, and the necessity to carry out all the steps under reduced pressure makes the process more expensive. Furthermore, in this process, considerable disadvantages arise upon application to a large industrial scale.

The known processes which are suitable for application to a large industrial scale operate batchwise In them, the necessary molar ratios required for uniform product quality can only be put into practice with difficulty on a large industrial scale. Thus, a less than equivalent amount of the amine of the compounds of the general formula II substantially reduces the yield of imidazoline compounds and promotes the undesired trisamide formation of the general formula X, due to an excess of fatty acids. If, on the other hand, the reaction is carried out with an excess of amine, it is difficult to maintain a constant and reproducible amine content particularly due to the vacuum distillation, so that an amine excess in the product and the distillate is present. This means substantial environmental pollution in large-scale processes.

Surprisingly, it has now been found that the present invention makes it possible to avoid the disadvantages of the previously known processes for the preparation of compounds of the general formulae (sic) I.

In the process according to the invention for the preparation of the 1-(acylaminoalkyl)-2-imidazolines substituted in the 2 position of the general formula I

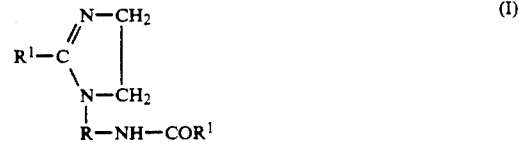

in which

R is an alkylene radical of the formula —CH$_2$CH$_2$—, —CH$_2$CH$_2$CH$_2$—, —CH(CH$_3$)CH$_2$— or —CH(CH$_3$)CH$_2$CH$_2$— and $R^1$ is a fatty acid radical of 7 to 25 C atoms, a fatty acid of the general formula II

or an ester of this fatty acid is reacted with a dialkylenetriamine of the general formula III

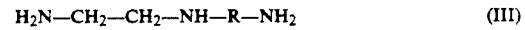

in which R and $R^1$ have the meanings already mentioned, at elevated temperature, in which process an acylation product of the dialkylenetriamine is first formed, which is then cyclized at elevated temperature under subatmospheric pressure, while distilling off the water, to give the compound of the formula I. The process according to the invention is characterized in that the fatty acid of the formula II or an ester thereof and the compound of the formula III are reacted in a molar ratio of (1.8 to 2.25):1 by initially introducing one educt at a temperature of $T_1$ and metering in the second educt in liquid form while maintaining the reaction mixture during the metering in at a temperature of $T_1$ and after the addition until the start of the cyclization at a temperature of $T_2$ and distilling off the water formed and/or the alcohol formed through a rectification column and, after the formation of the acylation product, carrying out the cyclization in a manner known per se, in which a) if a fatty acid of the formula II is used, $T_1$ is a temperature of 170° C. to 250° C., but at most up to the boiling point of the initially introduced educt, $T_2$ is a temperature of 170° to 250° C., and b) if an ester of the fatty acid is used, $T_1$ is a temperature of 100° to 250° C., at most up to the boiling point of the initially introduced educt and $T_2$ is a temperature of 100° to 250° C., at most up to the boiling point of the reaction mixture.

In the compounds of the formula I and II, the fatty acid radical $R^1$ of 7 to 25 C atoms is in particular an alkyl or alkenyl group. The alkyl and alkenyl groups can be straight-chain or branched and can also be substituted by OH. The alkenyl group can be mono- or polysaturated, for example di-, tri- or tetraunsaturated. The fatty acid radical $R^1$ is derived from fatty acids of 8 to 26 C atoms by elimination of the carboxyl group. Accordingly, suitable educts of the general formula II for the process according to the invention are fatty acids of 8 to 26 C atoms. Examples of such fatty acids are: caprylic acid, pelargonic acid, capric acid, undecanoic acid, lauric acid, myristic acid, palmitic acid, margaric acid, stearic acid, arachidic acid, behenic acid, lignoceric acid, cerinic acid, tuberculostearic acid, palmitoleic acid, oleic acid, ricinoleic acid, petroselic acid, vaccenic acid, linoleic acid, linolenic acid, elaeostearic acid, licanic acid, parinaric acid, arachidonic acid, erucic acid, selacholeic acid. Mixtures of these fatty acids can also be used, in particular mixtures of fatty acids such as can be obtained from solid, semisolid or liquid fats, for example coconut oil, palm kernel oil, olive oil, castor oil, rape oil, peanut oil, palm oil, lard or beef tallow. The technical grade fatty acid which is obtained from hardened beef tallow is particularly preferred.

The fatty acids of the general formula II can also be used in the form of their esters, in particular their alkyl esters of 1 to 4 C atoms, preferably their methyl or ethyl esters. In the context of the present invention, the esters are also understood to mean the glycerides, i.e. fats and oils. The alkyl esters and/or glycerides can also be used in mixtures with one another and/or in mixtures with the fatty acids.

The dialkylenetriamine of the general formula III which can be used is the diethylenetriamine of the formula XII

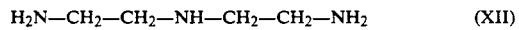
$$H_2N-CH_2-CH_2-NH-CH_2-CH_2-NH_2 \quad (XII)$$

or the triamine of the formula XIII

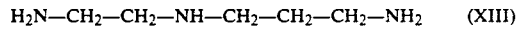
$$H_2N-CH_2-CH_2-NH-CH_2-CH_2-CH_2-NH_2 \quad (XIII)$$

or the triamine of the formula XIV

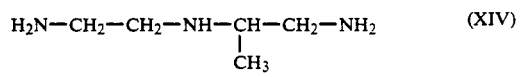
$$H_2N-CH_2-CH_2-NH-\underset{\underset{CH_3}{|}}{CH}-CH_2-NH_2 \quad (XIV)$$

or the triamine of the formula XV

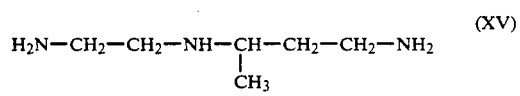
$$H_2N-CH_2-CH_2-NH-\underset{\underset{CH_3}{|}}{CH}-CH_2-CH_2-NH_2 \quad (XV)$$

The compounds of the formulae XII and XIII are known. The triamines of the formulae XIV and XV can be industrially produced by the addition reaction of monoacetylated ethylenediamine with methacrylonitrile or by the addition reaction of ethylenediamine with crotononitrile, followed by hydrogenation. It is also possible to use mixtures of these four triamines. The ethylene radical ($-CH_2CH_2-$) is preferred as R, which means that the diethylenetriamine of the formula XII is preferably used as the starting material of the general formula III.

The process according to the invention is carried out in a reaction vessel equipped with a fitted rectification column and advantageously a stirrer, and the entire reaction is advantageously carried out with stirring and under an inert gas atmosphere.

When the process according to the invention is carried out, an educt having a temperature of $T_1$ is initially introduced into a suitable reaction vessel. The initially introduced educt can be a fatty acid of the formula II or a ester of a fatty acid of the formula II or a dialkylenetriamine of the formula III.

The second educt is then added to the initially introduced educt in liquid form by metering, as a rule, the second educt into the initially introduced first educt as rapidly as possible.

If the initially introduced first educt is a fatty acid of the formula II or an ester of this fatty acid, the second educt is a dialkylenetriamine of the formula III. If the initially introduced first educt is a dialkylenetriamine of the formula III the second educt added is a fatty acid of the formula II or an ester (alkyl ester or glyceride) thereof.

The procedure in which a dialkylenetriamine of the formula III, in particular diethylenetriamine, is initially introduced as first educt is preferred, in particular if a fatty acid of the formula II is metered in as second educt. Preferably, the fatty acid of the formula II is metered in at at least the temperature of the initially introduced dialkylenetriamine.

If the reaction is carried out using a fatty acid of the formula II, the temperature $T_1$ at which the first educt is initially introduced and which is maintained in the reaction mixture during the addition of the second educt is 170° C. to 250° C., but at most the boiling point of the initially introduced educt, preferably 180° C. to 250° C., but at most up to boiling point of the initially introduced educt, and very particularly preferably 190° C. to 220° C., but at most up to the boiling point of the initially introduced educt.

The fatty acids of the formula II which are suitable as educts in most cases have a boiling point at atmospheric pressure of more than 250° C. A fatty acid of the formula II, such as, for example, stearic acid, which boils at atmospheric pressure above 250° C. is therefore initially introduced at a temperature of 170° to 250° C., preferably 180° to 250° C., and very particularly preferably 190° to 220° C.

Of the dialkylenetriamines of the formula III, diethylenetriamine boils at 207° C. A dialkylenetriamine of the formula II (sic) as the initially introduced first educt in the process according to the invention is used at a temperature of 170° C. to 250° C., at most up to the boiling point of the educt, preferably 180° C. to 250° C. at most up to the boiling point of the educt, and very particularly preferably 190° C. to 220° C., at most up to the boiling point of the educt.

The temperature $T_2$ which is maintained after the addition of the second educt up to the beginning of the cyclization is 170° to 250° C., preferably 180° to 250° and very particularly preferably 190° to 230° C., if a fatty acid of the formula II is used.

If an ester of a fatty acid of the formula II is used, the temperature $T_1$ at which the first educt is initially introduced and which is maintained in the reaction mixture during the addition of the second educt is 100° to 250° C., but at most up to the boiling point of the initially introduced educt, preferably 100° to 170° C., in particular 100° to 160° C., and very particularly preferably 110° to 150° C.

If an ester of a fatty acid of the formula II is used, the temperature $T_2$ which is maintained after the addition of the second educt is 100° to 250° C., at most up to the boiling point of the reaction mixture, preferably 100° to 170° C., in particular 100° to 160° C., and very particularly preferably 110° to 150° C.

The molar ratio of the fatty acid of the formula II or an ester of this fatty acid to the dialkylenetriamine of the formula III is (1.8 to 2.25):1, preferably (1.8 to 2.0):1, very particularly preferably (1.9 to 2.0):1. If an ester, in particular a glyceride, of a fatty acid of the formula II is used, the molar ratio of this ester to the dialkylenetriamine of the formula III is preferably (1.9 to 2.1):1.

The second educt is added to the first educt initially introduced at the temperature $T_1$ in liquid form, i.e. a second educt which is solid under standard conditions, such as, for example, some fatty acids, is melted before the addition. The temperature at which the second educt is added can range from the melting point of the second educt up to $T_2$, at most up to the boiling point of the second educt. If the second educt is added to the initially introduced first educt at a temperature which is below the temperature $T_1$, it may be necessary to ensure by adding heat that the temperature $T_1$ is maintained in the reaction mixture during the addition of the second educt.

Advantageously, the second educt is metered in in liquid form at a temperature which corresponds at least to the temperature of the initially introduced first educt and at most to the maximum temperature $T_2$, but is not higher than the boiling temperature of the second educt added.

It is particularly preferred to meter in the second educt at a temperature which is 0° to 25° C., preferably 5° to 25° C., very particularly preferably 5° to 15° C., above the temperature of the initially introduced first educt. This is preferred especially if the initially introduced first educt is a dialkylenetriamine of the formula III, in particular diethylenetriamine. The dialkylenetriamine, in particular the diethylenetriamine, is then initially introduced preferably at a temperature $T_1$ of 190° to 200° C., if a fatty acid of the formula II is used, and preferably at a temperature $T_1$ of 110° to 130° C., if an ester of the fatty acid of the formula II is used, and the second educt is metered in at a temperature which is 0° to 25° C., preferably 5° to 25° C., very particularly preferably 5° to 15° C., higher but not more than the boiling temperature of the second educt.

It is furthermore advantageous to raise the temperature in the reaction mixture, after the second educt has been metered in, until the beginning of the cyclization by 0° to 30° C., preferably 0° to 20° C.

In any case, it must be ensured, if necessary by adding or removing heat, that the temperature $T_1$ in the reaction mixture during the addition of the second educt and the temperature $T_2$ after the addition of the second educt are maintained until the beginning of the cyclization.

If the temperature of the metered-in second educt is higher than the temperature of the initially introduced first educt, the temperature in the reaction mixture during the preferred adiabatic operation increases during the addition of the second educt from the temperature of the first educt to the temperature of the second educt.

Immediately after the metering in of the second educt has started, amidoamine formation with the liberation of water (if a fatty acid of the formula II is used) or with the liberation of an alcohol sets in. This alcohol is an alkanol, if an alkyl ester of the fatty acid of the formula II is used, and is glycerol, if a glyceride of the fatty acid of the formula II is used.

Examples of suitable rectification columns are plate columns, columns containing packing, but in particular packed columns. The packing materials can be made, for example, of metal, ceramics or plastic Examples of suitable packing materials are Raschig rings, Pall rings, Berl saddles, Novalox saddles, Interpack packings and the like. Plate columns can contain, for example, bubble plates, perforated plates, valve plates or perforated-slotted plates. Packings for columns can be, for example, gauze packings, grid packings or diamond grid packings. The rectification column is designed and operated in a manner known per se, i.e. maintaining a temperature at the head of the column, while distilling off the water or the alcohol, which is 0° to 10° C., preferably 0° to 5° C., very particularly preferably 0° to 3° C., above the boiling point of the water or the alcohol. In order to establish these temperatures at the head of the column in practical operation, reflux ratios of up to 5, in most cases 3 to 4, are necessary at the beginning of the reaction. As the reaction proceeds, the reflux ratio can be reduced.

The reflux in the rectification column recycles other volatile reaction components, except for the water eliminated or the alcohol eliminated, into the reaction batch. The water or alcohol eliminated is distilled off via the rectification column in such a manner that, as far as possible, few other volatile compounds, in particular the educt of the formula III, are distilled off as well.

The reaction is preferably carried out with stirring and under an inert gas atmosphere. A suitable inert gas is any gas which does not react under the reaction conditions described with the starting material and the final product. Examples of suitable inert gases are, apart from nitrogen, noble gases such as neon, crypton and argon, nitrogen being preferred in particular because of its low price.

The metering rate during the addition of the second educt can be, depending on the design of the rectification column, set to such a high value that the addition is carried out within the shortest possible time of, for example, 5 to 60 minutes, so that only low amine contents are found in the distillate and the molar ratios can also be maintained exactly in the technical sector. Subsequent addition of one of the components, such as, for example, in the process of DE-A 3,620,218, can be entirely omitted.

It is assumed that before the start of the cyclization the amidoamine of the formula VIII is predominantly present. To promote the quantitative formation of this compound or to promote complete removal of the alcohol formed and in particular the water formed, as a rule it is advantageous to slowly reduce the pressure in the reaction vessel, immediately or some time after the addition of the second educt. The pressure can be reduced from atmospheric pressure, for example to 300 to 1 mbar, preferably 200 to 1.5 mbar. A slow reduction in the pressure usually takes place over a period of up to 1 hour.

The alcohol formed or the water formed is also distilled off through the rectification column during the reduction in pressure. During this distillation, a temperature which is 0° to 10° C., preferably 0° to 5° C., and very particularly preferably 0° to 3° C. above the boiling point of the alcohol or water to be distilled off and the particular pressure is maintained at the head of the column. Eliminated high-boiling alcohols, in particular eliminated glycerol, are in principle distilled off at reduced pressure.

The subsequent cyclization is carried out in a manner known per se at a subatmospheric pressure of at least 50 mbar, for example at a subatmospheric pressure of 50 to 0.01 mbar, preferably at 50 to 0.1 mbar. During the cyclization, a temperature of at least 140° C., in particular at least 170° C., preferably at least 190° C., is usually maintained. The cyclization can be carried out, for example, in the temperature range of 140° to 270° C., in particular 190° to 260° C. During the cyclization, the water formed is usually distilled off by bypassing the rectification column. The cyclization is in most cases completed after 1 to 6 hours. However, yields of about 90% are already obtainable after cyclization times of about 10 to 15 minutes. When an eliminated high-boiling alcohol is distilled off, in particular glycerol, the cyclization is usually already carried out during the distilling off, so that a mixture of high-boiling alcohol and water, in particular glycerol and water, is distilled off from the reaction vessel, which mixture is separated in the rectification column into very pure water which goes over first and into very pure high-boiling alcohol, in particular very pure glycerol, which goes over next.

To obtain light-coloured or colourless compounds of the general formula I, it is advantageous, if a fatty acid of the formula II is used, to carry out the process according to the invention in the presence of 0.2 to 5% by weight of phosphorous and/or hypophosphorous acid, relative to the total weight of the educts of the formulae II and III. This phosphorous and/or hypophosphorous acid can be added, if desired in the form of aqueous solutions, not only to the initially introduced dialkylenetriamine of the general formula III but also to the fatty acid of the general formula II. It is also possible to divide the amount used of the phosphorous and/or hypophosphorous acid between both starting materials of the formula II and III. The use of hypophosphorous acid is preferred.

If a fatty acid ester is used instead of the fatty acid of the general formula II, it is advantageous, in order to accelerate the reaction, to add, relative to the ester used about 0.01 to 0.2%, usually 0.03 to 0.5%, of a strong base, such as, for example, an alkali metal alcoholate, such as, for example, sodium methoxide or potassium methoxide or lithium methoxide, sodium ethoxide or potassium ethoxide or lithium ethoxide, sodium n-propoxide or potassium n-propoxide or lithium n-propoxide, sodium i-propoxide or potassium i-propoxide or lithium i-propoxide or sodium tert.-butoxide or potassium tert.-butoxide or lithium tert.-butoxide or an alkali metal hydroxide, such as, for example, lithium hydroxide, sodium hydroxide or potassium hydroxide. This base is usually added to the educt of the formula III. In contrast to the previous batchwise processes, the process according to the invention operates semi-continuously, in that the formation of the acylation product sets in as soon as the metering-in of the second educt is started with the elimination of water or alcohol.

In the process according to the invention, the escaping water and/or alcohol formed during the reaction does not cause any foaming or spattering or other difficulties. The overall reaction times have an average of 1 to 9 hours, in many cases 1 to 7 hours, are relatively short and thus allow space-time yields which are superior to the previous processes In many cases, overall reaction times of less than 1 hour down to, for example, about 15 minutes are possible.

The use of the rectification column in the process according to the invention ensures in particular that educts distilling out of the reaction vessel can be recycled again into the reaction mixture, so that in the reaction mixture, for example, no depletion of the dialkylenetriamine which is volatile in steam takes place. This makes it possible to carry out the reaction without any undesirable shifting of the molar ratios between the reactants and without a solvent. Especially because of that, the yields of the compounds of the general formula I are high and are usually 90 to 100% of theory, and the compounds of the formula I preparable by the process according to the invention are of such purity that they can be directly used further for a wide range of purposes without any further purification or aftertreatment operations. The imidazoline compounds of the formula I preparable by the process according to the invention in particular have a negligible content of the particularly undesirable trisamido compounds of the general formula X. The use of the rectification column in the process according to the invention makes it possible to obtain very pure waste water which is virtually free of amines. When glycerides or fats or oils are used, the use of the rectification column in the process according to the invention furthermore makes it possible to separate the water and glycerol formed in the reaction to such an extent that the separated water contains a maximum of 1 to 2% of glycerol, in many cases a maximum of 1% of glycerol, and the separated glycerol consists of 95%, in many cases at least 98%, of glycerol.

Examples 1 to 6 and 10 and 11 which follow refer to the process according to the invention. Examples 7 to 9 which follow are comparative examples which show that procedures not according to the invention only give substantially reduced yields and less pure products. The percentages given are by weight, unless stated otherwise. The yields given of the products of the formula I have been calculated from the tertiary nitrogen content of the product.

EXAMPLE 1

A 3-1 multi-neck flask equipped with stirrer, thermometer, manometer, magnetic control valve and rectification column is made inert by means of nitrogen 238 g (2.31 mol) of diethylenetriamine and 2.4 g (18 mmol) of hypophosphorous acid (as a 50% strength by weight aqueous solution) are then initially introduced and heated to 195° C. 1213 g (4.38 mol, calculated from the acid number) of stearic acid, which were preheated to 210° C., are metered in from a reservoir over a period of 18 minutes. During the addition, the temperature in the reaction mixture rises from 195° C. to 210° C. and is maintained at 210° C.

Distillation of the water of the reaction sets in spontaneously. In the column, the reflux ratio is set to 3 and the limiting column head temperature to 102° C. As the reaction proceeds, the reflux ratio is reduced to 1. To promote the water discharge further, 5 minutes after the addition of stearic acid is completed, the pressure in the flask is slowly reduced. After one hour, a pressure of 2 mbar has been reached. From this moment, the water of the reaction is discharged via a cold trap, while bypassing the column, and the cyclization is carried out at a temperature of 210° C. for 180 minutes.

Yield: 98% of 1-(2-stearoylaminoethyl)-2-heptadecyl-2-imidazoline. The diethylenetriamine content is less than 100 ppm.

EXAMPLE 2

Example 1 is repeated, except that the diethylenetriamine and the hypophosphorous acid are heated to 190° C., and the stearic acid is metered in at a temperature of 205° C. over a period of 15 minutes. The temperature in the reaction mixture is maintained at 200° C. After a pressure of 2 mbar has been reached, the cyclization is carried out at a temperature of 210° C. for 360 minutes.

Yield: 100% of 1-(2-stearoylaminoethyl)-2-heptadecyl-2-imidazoline. The diethylenetriamine content is less than 100 ppm.

EXAMPLE 3

In a 300 l stirred boiler flushed with nitrogen, 35.4 kg (0.34 kmol) of diethylenetriamine and 0.36 kg of hypophosphorous acid (as 50% strength by weight aqueous solution) are heated to 195° C. Over a period of 1.5 hours, 180 kg (0.65 kmol, calculated from the acid number) of stearic acid are metered in from a reservoir at a temperature of 200° C. The water of the reaction was liberated spontaneously and distilled off at a column head temperature of 100° to 102° C. through a rectification column (diameter:0.1 m, height: 1 m) packed with ceramics at a reflux ratio of 3 to 4. The distillate obtained is as clear as water and contains only 0.2% by weight of diethylenetriamine. During the addition, the boiler temperature increases from 195° to 200° C. After all of the stearic acid has been added, the boiler temperature is increased to 210° C. To promote the water discharge, the pressure is reduced from 1013 mbar to 150 mbar over a period of 1 hour. The pressure is then reduced to less than 10 mbar, and the cyclization is carried out at a temperature of 210° C., during which the water is distilled off, while bypassing the column.

The yield of 1-(2-stearoylaminoethyl)-2-hepetadecyl-2-imidazoline and the residual diethylenetriamine content during the course of the cyclization are as follows:

| Cyclization time in h | Yield of I in % | Residual diethylenetriamine content in ppm |
|---|---|---|
| 4 | 98 | <200 |
| 6 | 99 | <100 |

EXAMPLE 4

34.2 kg of diethylenetriamine (0.33 kmol) and 0.36 kg of hypophosphorous acid (as a 50% strength by weight aqueous solution) are initially introduced into the apparatus of Example 3 and heated to 195° C. Over a period of 1 hour, 180 kg (0.65 kmol, calculated from the acid number) of stearic acid are metered in from the reservoir at a temperature of 220° C. The spontaneously liberated water of the reaction is rectified at a column head temperature of 100° to 102° C. through the packed column. The distillate is as clear as water and contains 0.3% of diethylenetriamine. During the addition, the boiler temperature increases from 195° C. to 220° C. After all of the stearic acid has been added, the boiler temperature is increased to 230° C., and the pressure is reduced from 1013 mbar to 150 mbar over a period of 1 hour. The vacuum is then reduced directly to less than 10 mbar, while bypassing the column, and the boiler temperature is increased to 255° C.

The yield of 1-(2-stearoylaminoethyl)-2-heptadecyl-2-imidazoline and the residual diethylenetriamine content during the course of the cyclization are as follows:

| Cyclization time in h | Yield of I in % | Residual diethylenetriamine content in ppm |
|---|---|---|
| 1 | 93 | <100 |
| 2 | 94 | <100 |
| 4 | 95 | <100 |

EXAMPLE 5

Example 4 is repeated, except that the stearic acid and the hypophosphorous acid are initially introduced at a temperature of 200° C., and the diethylenetriamine is added at a temperature of 185° C. over a period of 1 hour from the reservoir, in the course of which the reaction temperature is increased to up to 220° C.

The yield of 1-(2-stearoylaminoethyl)-2-heptadecyl-2-imidazoline and the residual diethylenetriamine content during the course of the cyclization are as follows:

| Cyclization time in h | Yield of I in % | Residual diethylenetriamine content in ppm |
|---|---|---|
| 2 | 92 | <100 |
| 4 | 94 | <100 |

EXAMPLE 6

A 3-1 multi-neck flask equipped with anchor stirrer, thermometer, manometer, magnetic control valve and rectification column is made inert with nitrogen. 148.4 g (1.438 mol) of diethylenetriamine and 0.72 g of hypophosphorous acid (as a 50% strength by weight aqueous solution) are initially introduced and heated to an internal temperature of 200° C. 804.2 g of a technical grade arachidic/behenic acid mixture (2.74 mol) having an acid number of 191 are then metered in from a reservoir heated to 210° C. over a period of 20 minutes.

At a reflux ratio of 2 in the rectification column, the water formed is distilled off at a column head temperature of 102° C. The temperature in the reaction mixture increases during the addition from 200° C. to 210° C.

5 to 10 minutes after the addition of the behenic/arachidic acid mixture is completed, the pressure in the reaction flask is reduced to 2 mbar and, while bypassing the column, and the cyclization is carried out at a reaction temperature of 210° C. for 180 minutes.

Yield: 96% of an imidazoline mixture of the formula I. Residual dimethylenetriamine content: <100 ppm.

EXAMPLE 7

A 2-1 multi-neck flask equipped with anchor stirrer, thermometer, manometer, magnetic control valve and rectification column is made inert by means of nitrogen. 103 g (1 mol) of diethylenetriamine are then initially introduced, 2.86 g of 10% strength methanolic sodium methoxide solution are added, and the mixture is heated to 120° C., while passing in nitrogen. As soon as the temperature has reached 120° C., 568 g (1.93 mol) of methyl stearate are added from a heated reservoir at a temperature of 130° C. over a period of 20 minutes, and the methanol formed is distilled off through the rectification column at a column head temperature of 64° C. The cyclization is then carried out at a pressure of 2 mbar and a temperature of 191° C., while bypassing the column.

The yield of 1-(2-stearoylaminoethyl)-2-heptadecyl-2-imidazoline is:

| Cyclization time in min. | Yield in % |
| --- | --- |
| 10 | 90 |
| 20 | 95 |
| 60 | 98 |

EXAMPLE 8

Comparative Example

A 5-1 stainless steel pressure boiler equipped with a thermometer, anchor stirrer and plate valve is evacuated and flushed with nitrogen three times, and 0.222 kg (2.15 mol) of diethylenetriamine is initially introduced, and 1.215 kg (4.40 mol) of stearic acid are added in liquid form at a temperature of 70° to 75° C. Both reactants are then heated up, resulting in a paste which is difficult to stir. This paste becomes clear at 135° C., and at 145° to 150° C. the reaction sets in so violently that it can only be carried out at a superatmospheric pressure of up to 2 bar. After releasing the pressure, the cyclization is carried out at 170° to 190° C. and 10 mbar for 6 hours.

The starting molar ratio of stearic acid to diethylenetriamine is 2.05:1.

Yield: 84.9% of theory of 1-(2-stearoylaminoethyl)-2-heptadecyl-2-imidazoline, diethylenetriamine content > 500 pm, acid number: 5 (corresponds to 2.4% of free stearic acid).

EXAMPLE 9

Comparative Example

A 5-1 stainless steel pressure vessel equipped with a thermometer, anchor stirrer and plate valve is evacuated and flushed with nitrogen three times, and 1.5 kg (5.43 mol) of stearic acid are melted and heated together with 1.66 g of hypophosphorous acid to an internal temperature of 120° to 130° C. 295 g (2.86 mol) of diethylenetriamine are then injected at a temperature of 130° C. from a second 1-1 stainless steel pressure vessel. After 3 minutes, the reaction sets in violently with foaming, and a pressure of 1.5 bar is measured in the reaction vessel.

After releasing the pressure, the water is distilled off at a temperature of 150° to 170° C. through a descending condenser, and the cyclization is carried out at 180° to 190° C. at 10 mbar for 4 hours.

Starting molar ratio of stearic acid to diethylenetriamine = 1.89:1

Yield: 78.0% of theory of 1-(2-stearoylaminoethyl)-2-heptadecyl-2-imidazoline, diethylenetriamine content > 500 ppm. Acid number: 9.5 (corresponds to 3.44% of free stearic acid).

EXAMPLE 10

30.62 kg (0.297 kmol) of diethylenetriamine are initially introduced into a 300 liter stirred boiler flushed with nitrogen and heated to a temperature of 100° C. 180 kg (0.6258 kmol) of tallow fatty acid triglyceride having a saponification number of 195 are then metered in in liquid form at a temperature of 125° to 130° C. at a rate of 200 kg/h, resulting in an increase of the reaction temperature in the reaction boiler to 150° to 160° C. Any water formed as a distillate is separated from the glycerol and the amine at a limiting column head temperature of 100° C. through a rectification column.

At a reduced pressure of 100-5 mbar, water and glycerol are then distilled off through a rectification column. At a reflux ratio of 3, a distillate consisting of water containing 0.1-0.5% of glycerol and traces (less than 0.1%) of diethylenetriamine is obtained over a period of 1 hour at 100 mbar and 3 hours at 100-50 mbar and a boiler temperature of 190° C. At a pressure of 10-5 mbar, glycerol is then distilled off in a purity of 98-100% over a period of 6 hours. After this time, the cyclization is completed.

The wax-like slightly light yellow-brown product obtained contains at least 94% of the compounds of the formula I, in which R is —CH$_2$CH$_2$— and R$^1$ is mainly a (C$_{15}$ to C$_{17}$)-alkyl mixture, and the residual free diethylenetriamine content is less than 100 ppm, and the trisacylamide content is equal to or less than 4%.

EXAMPLE 11

29.0 kg (0.2816 kmol) of diethylenetriamine are initially introduced into a 300 liter stirred boiler flushed with nitrogen and heated to 150° C. 180 kg (0.6258 kmol) of hardened tallow having a saponification number of 195 and a temperature of 165° C. are then metered into this reaction boiler at a rate of 300 kg/h, resulting in an increase of the reaction temperature to 175° C. The reaction temperature is then increased to 210° C. as quickly as possible, and the pressure is continuously reduced to 20 mbar. Any water formed is separated from the glycerol and the amine at a reflux ratio of 2.5 through a rectification column, as a result of which the distillate contains 0.5-1% of glycerol and traces of diethylenetriamine.

Glycerol is then distilled off in a purity of at least 98 at a pressure of 20-5 mbar over a period of 6 hours.

The wax-like slightly light yellow-brown product obtained contains 95.5% of the compound of the formula I, where R is —CH$_2$CH$_2$— and R$^1$ is mainly a (C$_{15}$ to C$_{17}$)-alkyl mixture, the residual free diethylenetriamine content is less than 100 ppm and the trisacylamide content is equal to or less than 4%.

We claim:

1. Process for the preparation of 1-(acylaminoalkyl)-2-imidazolines substituted in the 2-position of the general formula I

in which

R is an alkylene radical of the formula —CH$_2$CH$_2$—, —CH$_2$CH$_2$CH$_2$—, —CH(CH$_3$)CH$_2$— or —CH(CH$_3$)CH$_2$CH$_2$— and R$^1$ is a fatty acid radical of 7 to 25 C atoms derived from a fatty acid by elimination of the carboxyl group, by reaction of a fatty acid of the general formula II

R$^1$COOH  (II)

and/or a glyceride and/or an ester of this fatty acid with a dialkylenetriamine of the general formula III

NH$_2$—(CH$_2$)$_2$—NH—R—NH$_2$  (III)

which R and R¹ have the abovementioned meanings, at elevated temperatures, in which an acylation product of the dialkylenetriamine is first formed, which is then cyclized at elevated temperature under subatmospheric pressure, while distilling off the water, to give the compound of the formula I, characterized in that the fatty acid of the formula II and/or a glyceride and/or an ester of this fatty acid and the compound of the formula III are reacted in a molar ratio of (1.8 to 2.25):1 by initially introducing an educt at a temperature of $T_1$ and metering in the second educt in liquid form, while maintaining a temperature of $T_1$ in the reaction mixture during the addition and a temperature of $T_2$ after the addition until the start of the cyclization and distilling off the water and/or the alcohol and/or the glycerol formed through a rectification column and, after the formation of the acylation product, carrying out the cyclization at a temperature of at least 140° C. and a subatmospheric pressure of at least 50 mbar in which a) if a fatty acid of the formula II is used, $T_1$ is a temperature of 170° C. to 250° C., but at most up to the boiling point of the initially introduced educt, $T_2$ is a temperature of 170° to 250° C., and b) if a glyceride or ester of the fatty acid is used, $T_1$ is a temperature of 100° to 250° C., at most up to the boiling point of the initially introduced educt and $T_2$ is a temperature of 100° to 250° C., at most up to the boiling point of the reaction mixture.

2. Process according to claim 1, characterized in that, if a fatty acid of the formula II is used, $T_1$ is a temperature of 180° C. to 250° C., but at most up to the boiling point of the initially introduced educt.

3. Process according to claim 1, characterized in that, if a fatty acid of the formula II is used, $T_2$ is a temperature of 180° to 250° C.

4. Process according to claim 1, characterized in that, if a glyceride or ester of the fatty acid II is used, $T_1$ is 100° to 250° C., but at most up to the boiling point of the initially introduced educt.

5. Process according to claim 1, characterized in that, if a glyceride or ester of the fatty acid II is used, $T_2$ is a temperature of 100° to 170° C.

6. Process according to claim 1, characterized in that a molar ratio of (fatty acid of the formula II or a glyceride or ester of this fatty acid) to the dialkylenetriamine of the formula III of (1.8 to 2.0):1 is maintained.

7. Process according to claim 1, characterized in that the second educt is metered in at at least the temperature of the initially introduced first educt and at most at the maximum temperature $T_2$, but not higher than the boiling temperature of the second educt metered in.

8. Process according to claim 1, characterized in that diethylenetriamine is initially introduced and stearic acid is metered in.

9. Process according claim 1, characterized in that, when the water or the alcohol or the glycerol is distilled off, a temperature is maintained at the column head which is 0° to 10° C. above the boiling point of the water or the alcohol or the glycerol.

10. Process according to claim 1, characterized in that the pressure in the reaction vessel is reduced to 300 to 1 mbar after the addition of the second educt.

11. Process according to claim 1, characterized in that, if a fatty acid of the formula II is used, the reaction is carried out in the presence of 0.2 to 5% of phosphorous acid, hypophosphorous acid and/or phosphoric acid, relative to the total weight of the educts of the general formulae II and III.

12. Process according to claim 1, characterized in that, if a glyceride or ester of a fatty acid of the formula II is used, the reaction is carried out in the presence of 0.01 to 5% of a strong base.

13. Process according to claim 1, characterized in that, if a fatty acid of the formula II is used, the dialkylenetriamine of the formula III is initially introduced at a temperature of 190° to 200° C. and, if a glyceride or ester of a fatty acid is used, at a temperature of 110° to 130° C., and the other educt is metered in at a temperature higher by 0° to 25° C.

14. Process according to claim 1, characterized in that a glyceride of the fatty acid of the formula II is used.

15. Process according to claim 1, characterized in that a glyceride of the fatty acid of the formula II is used and, at the end of the reaction, first water containing not more than 2% of glycerol and then glycerol containing at least 95% of glycerol are distilled off through the rectification column.

* * * * *